United States Patent
Ahn et al.

(10) Patent No.: US 10,473,579 B2
(45) Date of Patent: Nov. 12, 2019

(54) APPARATUS FOR INSPECTING MATERIAL PROPERTY OF PLURALITY OF MEASUREMENT OBJECTS

(71) Applicant: SAMSUNG ELECTRONICS CO., LTD., Suwon-si, Gyeonggi-Do (KR)

(72) Inventors: Tae-Heung Ahn, Seoul (KR); Young Duk Kim, Seongnam-si (KR); Sang Gil Park, Hwaseong-si (KR); Jun Bum Park, Goyang-si (KR); Yoichiro Iwa, Suwon-si (KR); Byeong Hwan Jeon, Yongin-si (KR)

(73) Assignee: SAMSUNG ELECTRONICS CO., LTD., Suwon-si, Gyeonggi-Do (KR)

( * ) Notice: Subject to any disclaimer, the term of this patent is extended or adjusted under 35 U.S.C. 154(b) by 0 days.

(21) Appl. No.: 15/981,359

(22) Filed: May 16, 2018

(65) Prior Publication Data

US 2019/0079003 A1    Mar. 14, 2019

(30) Foreign Application Priority Data

Sep. 14, 2017    (KR) ........................ 10-2017-0117983

(51) Int. Cl.
| | |
|---|---|
| *G01N 21/01* | (2006.01) |
| *G01N 21/17* | (2006.01) |
| *H01L 21/67* | (2006.01) |
| *G01N 21/94* | (2006.01) |

(Continued)

(52) U.S. Cl.
CPC ......... *G01N 21/01* (2013.01); *G01N 15/1434* (2013.01); *G01N 21/17* (2013.01);

(Continued)

(58) Field of Classification Search
CPC ....... G01N 15/1434; G01N 2015/1493; G01N 21/01; G01N 21/17; G01N 21/94;

(Continued)

(56) References Cited

U.S. PATENT DOCUMENTS

| | | |
|---|---|---|
| 8,305,574 B2 | 11/2012 | Arimoto et al. |
| 2004/0189979 A1 | 9/2004 | Fujimura et al. |

(Continued)

FOREIGN PATENT DOCUMENTS

| | | |
|---|---|---|
| JP | 07-120393 | 5/1995 |
| JP | 4217108 | 11/2008 |

(Continued)

*Primary Examiner* — Tri T Ton (74) *Attorney, Agent, or Firm* — F. Chau & Associates, LLC (57) ABSTRACT

An inspection apparatus includes a light source. A first measurement unit is configured to receive light from the light source and direct it to a first measurement object. A second measurement unit is configured to receive the light from the light source and direct it to a second measurement object. An inspection unit is configured to receive a first optical signal provided from the first measurement unit and inspect the first measurement object using the first optical signal, and to receive a second optical signal provided from the second measurement unit and inspect the second measurement object using the second optical signal. A measurement position selection unit is configured to alternately enable the inspection of the two measurement units by adjusting an angle of a reflection mirror.

14 Claims, 9 Drawing Sheets

(51) Int. Cl.
  *G01N 15/14* (2006.01)
  *G01N 21/88* (2006.01)
  *G01N 21/95* (2006.01)
  *G01N 21/84* (2006.01)
(52) U.S. Cl.
  CPC ......... *G01N 21/8806* (2013.01); *G01N 21/94* (2013.01); *H01L 21/67288* (2013.01); *G01N 21/9501* (2013.01); *G01N 2015/1493* (2013.01); *G01N 2021/8427* (2013.01); *G01N 2201/0636* (2013.01); *G01N 2201/0638* (2013.01); *G01N 2201/0666* (2013.01); *G01N 2201/084* (2013.01)
(58) Field of Classification Search
  CPC ... G01N 2201/0636; G01N 2201/0638; G01N 2201/0666; G01N 2201/084; H01L 21/67288

USPC .............. 356/335–343, 124.5–137, 244–255
See application file for complete search history.

(56) References Cited

U.S. PATENT DOCUMENTS

2008/0285032 A1\* 11/2008 Ohkubo ............. G01N 15/0205
  356/343
2013/0273670 A1  10/2013 Arimoto et al.

FOREIGN PATENT DOCUMENTS

| JP | 2016164534 | 9/2016 |
| KR | 101072434 | 10/2011 |
| KR | 20130116190 | 10/2013 |

\* cited by examiner

APPARATUS FOR INSPECTING MATERIAL PROPERTY OF PLURALITY OF MEASUREMENT OBJECTS

This application claims priority from Korean Patent Application No. 10-2017-0117983 filed on Sep. 14, 2017 in the Korean Intellectual Property Office, the disclosure of which is incorporated by reference herein in its entirety.

TECHNICAL FIELD

The present application relates to an inspection apparatus and, more specifically, to an apparatus for inspecting a material property of a plurality of measurement objects.

DISCUSSION OF THE RELATED ART

In general, semiconductor devices are manufactured through a fabrication ("fab") process in which an electric circuit including electric components are formed on a silicon wafer, which is used as a semiconductor substrate. After fabrication, an electrical die sorting (EDS) process may be performed for inspecting electric characteristics of semiconductor devices formed in the Fab process. A package assembly process may then be performed for encapsulating each of the semiconductor devices with an epoxy resin and individualizing the semiconductor devices.

The fab process generally includes a deposition process by which a film is formed on a semiconductor substrate. A chemical mechanical polishing process is performed for smoothing the film. A photolithography process is performed for forming a photoresist pattern on the film. An etching process is performed for forming the film as a pattern having electric characteristics using the photoresist pattern. An ion injection process is performed for injecting a specific ion into a predetermined region of the semiconductor substrate. A cleaning process is performed for removing impurities from the semiconductor substrate. An inspection process is performed for inspecting a surface of the semiconductor substrate on which the film or pattern is formed.

Defects of the semiconductor substrate, such as foreign substances remaining on the semiconductor substrate, may degrade operation performance and productivity of the semiconductor device.

SUMMARY

An inspection apparatus includes a light source generating a first light. A first measurement unit is configured to receive the first light from the light source and direct the first light to a first measurement object. A second measurement unit is configured to receive the first light from the light source and direct the first light to a second measurement object which is different from the first measurement object. An inspection unit is configured to receive a first optical signal provided from the first measurement unit along a first optical path and inspect the first measurement object using the first optical signal, and to receive a second optical signal provided from the second measurement unit along a second optical path that is different from the first optical path and inspect the second measurement object using the second optical signal. A measurement position selection unit is configured to alternatively enable the first and second optical paths by adjusting an angle of a reflection mirror.

An inspection apparatus includes a first measurement unit in which a first measurement object is disposed. The first measurement unit comprises a first illumination unit configured to provide a first light to the first measurement object, and a first light receiving unit configured to receive the first light passing through the first measurement object. A second measurement unit, in which a second measurement object is disposed, comprises a second illumination unit configured to provide a second light to the second measurement object, and a second light receiving unit configured to receive the second light passing through the second measurement object. An inspection unit is configured to receive a first optical signal provided from the first measurement unit and inspect the first measurement object therefrom, and to receive a second optical signal provided from the second measurement unit and inspect the second measurement object therefrom. A reflection mirror is configured to direct either of the first or second optical signals to the inspection unit. A control unit is configured to control a driving unit to adjust an angle of the reflection mirror.

An inspection apparatus includes a first measurement unit configured to direct a light into a first measurement object. A second measurement unit is configured to direct the light into a second measurement object. An inspection unit is configured to inspect the first measurement object and inspect the second measurement object. A measurement position selection unit is configured to alternatively provide a first optical signal from the first measurement unit to the inspection unit and a second optical signal from the second measurement unit to the inspection unit, by adjusting an angle of a reflection mirror.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Hereinbelow, an apparatus for inspecting a material property according to some exemplary embodiments of the present disclosure will be described with reference to FIG. 1.

Figure 1:
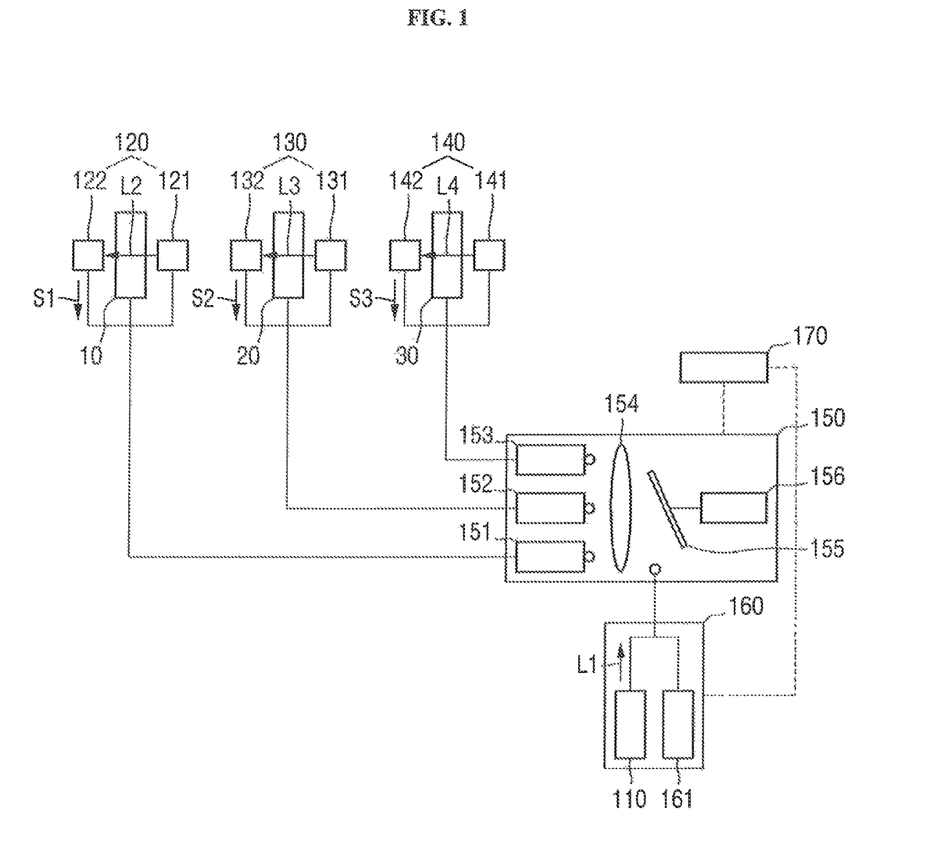
FIG. 1 is a schematic diagram illustrating an apparatus for inspecting a material property according to some exemplary embodiments of the present disclosure.

FIG. 1 is a schematic diagram illustrating an apparatus for inspecting a material property according to some exemplary embodiments of the present disclosure.

The apparatus for inspecting the material property according to some exemplary embodiments of the present disclosure may be used to inspect properties of materials of a semiconductor substrate at each step of the manufacturing process of semiconductor devices. For example, inspection may occur at a deposition process for forming a film, a chemical mechanical polishing process for smoothing the film, a photolithography process for forming a photoresist pattern on the film, an etching process for forming a pattern using the photoresist pattern, an ion injection process for injecting a specific ion to a predetermined region of the semiconductor substrate, and a cleaning process for removing impurities. However, the present disclosure is not limited thereto.

Referring to FIG. 1, the apparatus for inspecting the material property according to some exemplary embodiments of the present disclosure includes a light source 110, a first measurement unit 120, a second measurement unit 130, a third measurement unit 140, a measurement position selection unit 150, an inspection unit 160 that may include the aforementioned light source 110, and a control unit 170.

The light source 110 may provide first light (L1) to each of the first measurement unit 120, the second measurement unit 130, and the third measurement unit 140.

For example, the light source 110 may provide the first light (L1) to a first head 151 connected to the first measurement unit 120, a second head 152 connected to the second measurement unit 130, and/or a third head 153 connected to the third measurement unit 140. The determination as to which of the heads 151, 152, and 153 receives the light (L1) from the light source 110 may be determined according to an angle of a reflection mirror 155 that is disposed within the aforementioned measurement position selection unit 150.

The first light (L1) provided to the first head 151 may thereafter be provided to a first illumination unit 121 of the first measurement unit 120 through an optical fiber. The first light (L1) provided to the second head 152 may thereafter be provided to a second illumination unit 131 of the second measurement unit 130 through an optical fiber. The first light (L1) provided to the third head 153 may thereafter be provided to a third illumination unit 141 of the third measurement unit 140 through an optical fiber.

The light source 110 may provide the first light (L1) to the first illumination unit 121 when a first measurement object 10 is positioned in the first measurement unit 120. The light source 110 may provide the first light (L1) to the second illumination unit 131 when a second measurement object 20 is positioned in the second measurement unit 130. The light source 110 may provide the first light (L1) to the third illumination unit 141 when a third measurement object 30 is positioned in the third measurement unit 140.

Although FIG. 1 shows that the light source 110 is disposed within the inspection unit 160, the present disclosure is not limited thereto. For example, in some exemplary embodiments of the present disclosure, the light source 110 may be disposed outside of the inspection unit 160.

The first measurement unit 120 may include the first illumination unit 121 and a first light receiving unit 122.

The first illumination unit 121 may receive the first light (L1) from the light source 110, and may radiate a second light (L2) to the first measurement object 10. The first light receiving unit 122 may receive the second light (L2) that has passed through the first measurement object 10, and may then provide a first optical signal (S1) to the first head 151 through the optical fiber.

The second measurement unit 130 may include the second illumination unit 131 and a second light receiving unit 132.

The second illumination unit 131 may receive the first light (L1) from the light source 110, and may radiate a third light (L3) to the second measurement object 20. The second light receiving unit 132 may receive the third light (L3) that has passed through the second measurement object 20, and may then provide a second optical signal (S2) to the second head 152 through the optical fiber.

The third measurement unit 140 may include the third illumination unit 141 and a third light receiving unit 142.

The third illumination unit 141 may receive the first light (L1) from the light source 110, and may radiate a fourth light (LA) to the third measurement object 30. The third light receiving unit 142 may receive the fourth light (L4) that has passed through the third measurement object 30, and may provide a third optical signal (S3) to the third head 153 through the optical fiber.

Although FIG. 1 shows the use of three measurement units 120, 130, and 140, the present disclosure is not limited thereto. For example, in some exemplary embodiments of the present disclosure, four or more measurement units may be arranged.

The measurement position selection unit 150 may include the first head 151, the second head 152, the third head 153, a lens 154, the reflection mirror 155, and a driving unit 156. The driving unit 156 may be configured to adjust an angle of the reflection mirror 155 so as to direct the first light (L1) to a desired head of the first, second, and third heads 151, 152, and 153. In this regard, the driving unit 156 may be an actuator.

The measurement position selection unit 150 may be connected to the first measurement unit 120, the second measurement unit 130, and the third measurement unit 140, through the optical fibers connected to the first head 151, the second head 152, and the third head 153, respectively. In addition, the measurement position selection unit 150 may be connected to the inspection unit 160 through an optical fiber.

The measurement position selection unit 150 may provide the first light (L1) provided from the light source 110 to any one of the first measurement unit 120, the second measurement unit 130, and the third measurement unit 140.

In addition, the measurement position selection unit 150 may provide the first optical signal (S1) from the first measurement unit 120, the second optical signal (S2) from the second measurement unit 130, and/or the third optical signal (S3) from the third measurement unit 140, to the inspection unit 160.

The lens 154 may concentrate the first light (L1) provided from the light source 110 and reflected by the reflection mirror 155 onto the first head 151, the second head 152, and/or the third head 153.

In addition, the lens 154 may concentrate, on the reflection mirror 155, the first optical signal (S1) from the first light receiving unit 122, the second optical signal (S2) from the second light receiving unit 132, and/or the third optical signal (S3) from the third light receiving unit 142.

The reflection mirror 155 may have an angle thereof adjusted by the driving unit 156, thereby reflecting the first light (L1) provided from the light source 110 into the first head 151, the second head 152, and/or the third head 153.

In addition, the reflection mirror 155 may have the angle thereof adjusted by the driving unit 156, thereby reflecting the first optical signal (S1) from the first head 151, the second optical signal (S2) from the second head 152, and/or the third optical signal (S3) from the third head 153, into the inspection unit 160. This will be described in greater detail below.

The control unit 170 may control the driving unit 156 to adjust the angle of the reflection mirror 155. For example, the control unit 170 may provide the first optical signal (S1), the second optical signal (S2), and/or the third optical signal (S3) to the inspection unit 160 by adjusting the angle of the reflection mirror 155 by driving the driving unit 156 for a preset time.

However, the present disclosure is not limited thereto. For example, in some exemplary embodiments of the present disclosure, when a measurement object is positioned in the first measurement unit 120, the second measurement unit 130, and/or the third measurement unit 140, the control unit 170 may provide the first optical signal (S1), the second optical signal (S2), and/or the third optical signal (S3) to the inspection unit 160 by adjusting the angle of the reflection mirror 155, for example, by driving the driving unit 156.

The inspection unit 160 may include the light source 110 and a concentration measurement unit 161. However, the light source 110 may be disposed outside the inspection unit 160 as described above.

According to some embodiments, as can be seen from FIG. 1, a same optical fiber may be used to transmit light back and forth between the first measurement unit 120 and the inspection unit 160. Another optical fiber may be used to transmit light back and forth between the second measurement unit 130 and the inspection unit 160. Yet another optical fiber may be used to transmit light back and forth between the third measurement unit 140 and the inspection unit 160. In this way, there may be as many optical fibers as there are measurement objects, and also, according to this arrangement, there need only be one light source 110 and one concentration measurement unit 161, regardless of how many measurement objects and measurement units there are. However, the present disclosure is not limited thereto. For example, according to some other embodiments, as can be seen from FIG. 8, optical fibers to be used to transmit light back and forth may be different each other.

The single inspection unit 160 may thereby inspect a material property of each of the first measurement object 10, the second measurement object 20, and the third measurement object 30.

For example, the inspection unit 160 may inspect the material property of the first measurement object 10 by receiving the first optical signal (S1) from the first measurement unit 120, may inspect the material property of the second measurement object 20 by receiving the second optical signal (S2) from the second measurement unit 130, and may inspect the material property of the third measurement object 30 by receiving the third optical signal (S3) from the third measurement unit 140.

The inspection unit 160 may inspect a first material property of each of the first to third measurement objects 10, 20, and 30 and may also inspect a second material property, which is different from the first material property. For example, the first material property may be a concentration of a material included in each of the first to third measurement objects 10, 20, and 30, and the second material property may be a particle size included in each of the first to third measurement objects 10, 20, and 30.

However, the present disclosure is not limited thereto. For example, in some exemplary embodiments of the present disclosure, the inspection unit 160 may inspect three or more different material properties of each of the first to third measurement objects 10, 20, and 30.

Although FIG. 1 shows that the inspection unit 160 includes the concentration measurement unit 161 to inspect a concentration of a material included in each of the first to third measurement objects 10, 20, and 30, this is merely one of many possible examples, and the present disclosure is not limited thereto. For example, in some exemplary embodiments of the present disclosure, the inspection unit 160 may include a particle measurement unit to inspect a particle size included in each of the first to third measurement objects 10, 20, and 30.

Hereinafter, a method for inspecting a material property using an apparatus for inspecting a material property according to some exemplary embodiments of the present disclosure will be described with reference to FIG. 1 to FIG. 5.

Figure 2:
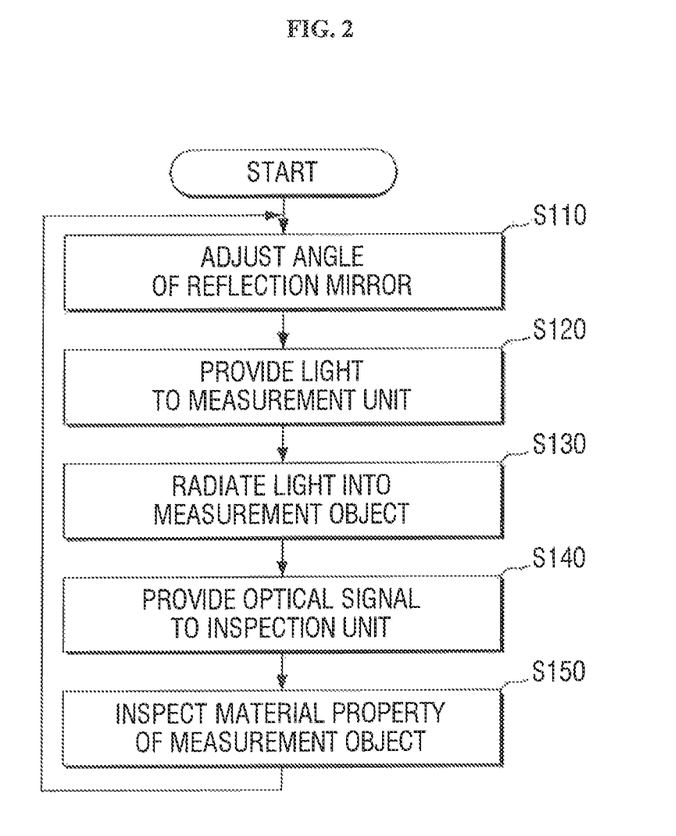
FIG. 2 is a flow chart illustrating a method for inspecting a material property using an apparatus for inspecting a material property according to some exemplary embodiments of the present disclosure.
Figure 3:
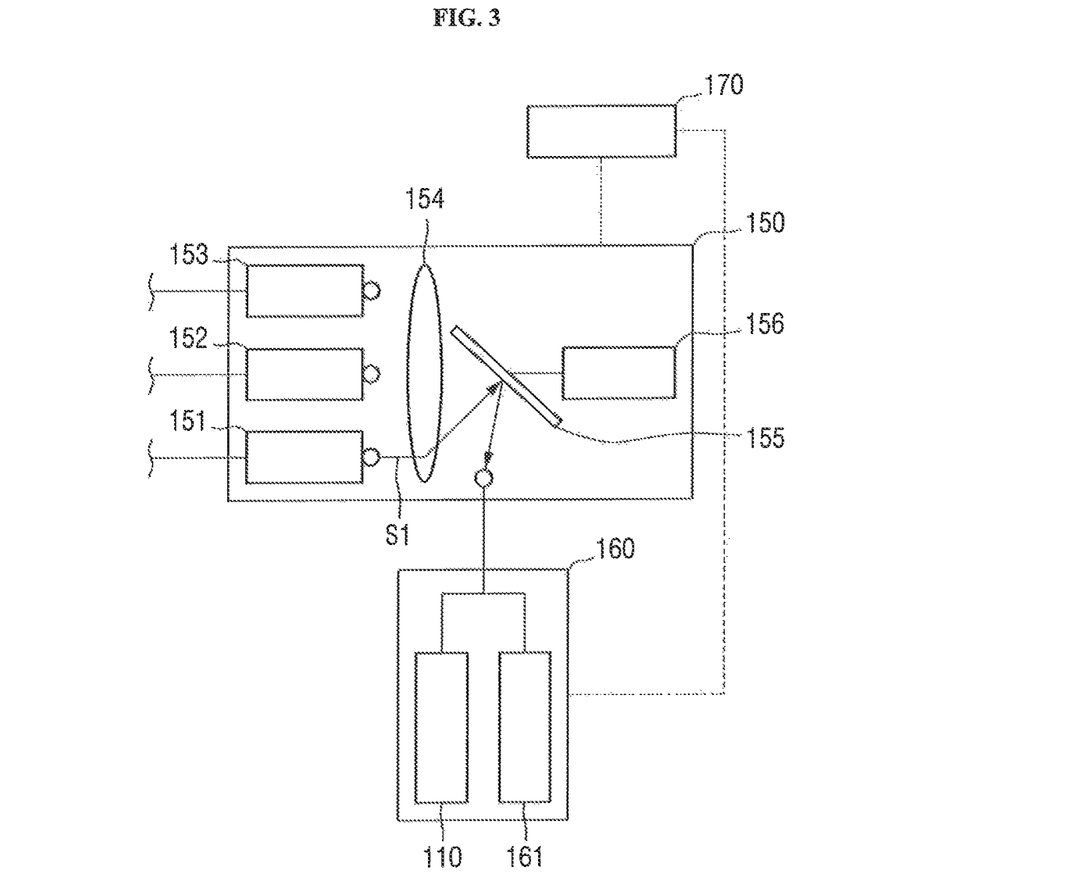
FIG. 3 to FIG. 5 are diagrams illustrating an operation of an apparatus for inspecting a material property according to some exemplary embodiments of the present disclosure.
Figure 4:
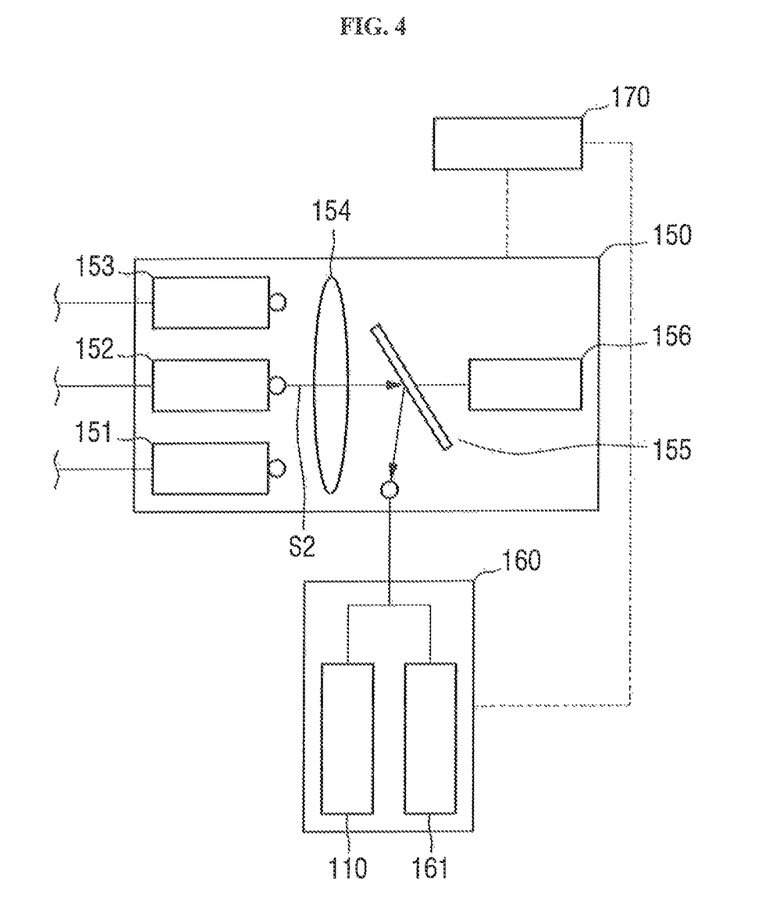
Figure 5:
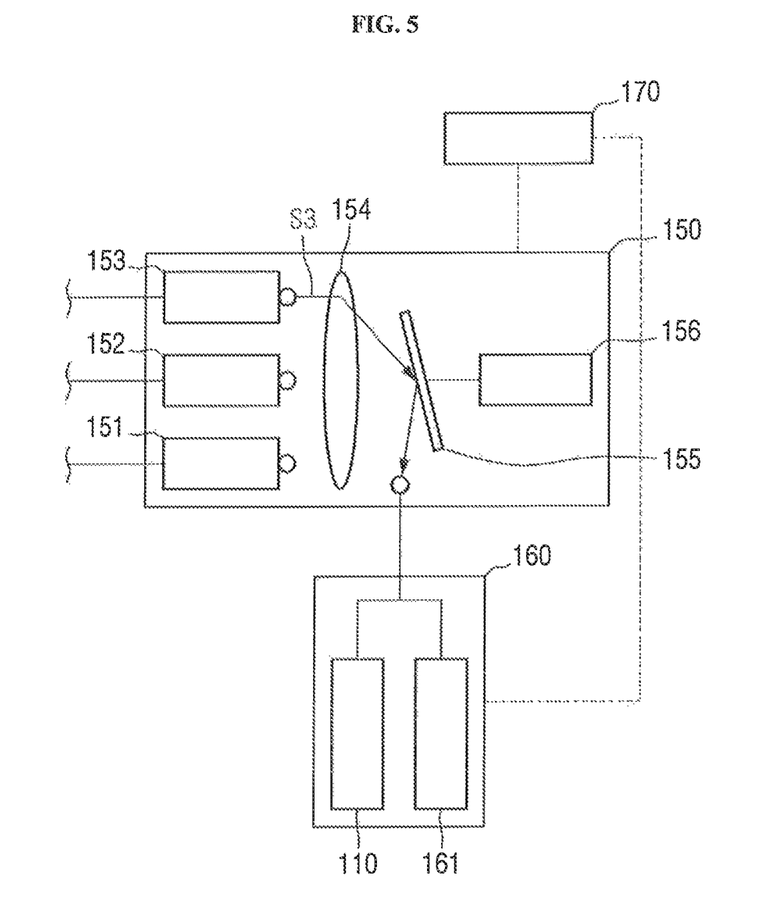

FIG. 2 is a flow chart illustrating a method for inspecting a material property using an apparatus for inspecting a material property according to some exemplary embodiments of the present disclosure. FIG. 3 to FIG. 5 are schematic diagrams illustrating an operation of an apparatus for inspecting a material property according to some exemplary embodiments of the present disclosure.

Referring to FIG. 1 to FIG. 3, when a material property of the first measurement object 10 positioned in the first measurement unit 120 is measured, the control unit 170 may adjust the angle of the reflection mirror 155, by driving the driving unit 156, in the manner shown in FIG. 3 (S110).

After the angle of the reflection mirror 155 is adjusted, the light source 110 may provide the first light (L1) to the first measurement unit 120 (S120).

For example, the first light (L1) provided from the light source 110 may be reflected by the reflection mirror 155 in such a way as to be provided to the first head 151. The first light (L1) provided to the first head 151 may be guided to the first illumination unit 121 of the first measurement unit 120 through the optical fiber.

The first illumination unit 121 may direct the second light (L2) into the first measurement object 10 (S130). Although light provided from the light source 110 is defined as the first light (L1) and light directed into the first measurement object 10 by the first illumination unit 121 is defined as the second light (L2), this is merely for the convenience of explanation, and the first light (L1) and the second light (L2) may be thought of as the same light.

The second light (L2) radiated from the first illumination unit 121 and passing through the first measurement object 10 may be received by the first light receiving unit 122. The first light receiving unit 122 may provide the first optical signal (S1) to the inspection unit 160 (S140).

For example, the first optical signal (S1) provided from the first light receiving unit 122 may be provided to the first head 151 through the optical fiber. The first optical signal (S1) provided to the first head 151 may be reflected by the reflection mirror 155, and may be provided to the inspection unit 160.

Accordingly, the first light (L1) and the first optical signal (S1) may both travel between the first head 151 and the first measurement unit 120 along the same optical fiber, which may be referred to herein as a first optical fiber. However, the present disclosure is not limited thereto.

The inspection unit 160 may inspect the material property of the first measurement object 10 using the first optical signal (S1) (S150). For example, the concentration measurement unit 161 arranged in the inspection unit 160 may inspect a concentration of a material included in the first measurement object 10 using the first optical signal (S1). The material property of the first measurement object 10 may be inspected according to the above-described process.

Referring to FIG. 1, FIG. 2, and FIG. 4, in order to inspect the material property of the second measurement object 20 positioned in the second measurement unit 130, the control unit 170 may adjust the angle of the reflection mirror 155 by driving the driving unit 156, as shown in FIG. 4 (S110).

After the angle of the reflection mirror 155 is adjusted, the material property of the second measurement object 20 may be inspected through a process similar to that when the material property of the first measurement object 10 is measured.

For example, after the angle of the reflection mirror 155 is adjusted, the light source 110 may provide the first light (L1) to the second measurement unit 130 (S120). The second illumination unit 131 may direct the third light (L3) into the second measurement object 20 (S130). The second light receiving unit 132 may provide the second optical signal (S2) to the inspection unit 160 (S140). The inspection unit 160 may inspect the material property of the second measurement object 20 using the second optical signal (S2) (S150). The material property of the second measurement object 20 may be inspected according to the above-described process.

Accordingly, the first light (L1) and the second optical signal (S2) may both travel between the second head 152 and the second measurement unit 130 along the same optical fiber, which may be referred to herein as a second optical fiber. The second optical fiber may be different form the first optical fiber. However, the present disclosure is not limited thereto.

Referring to FIG. 1, FIG. 2, and FIG. 5, to inspect the material property of the third measurement object 30 positioned in the third measurement unit 140, the control unit 170 may adjust the angle of the reflection mirror 155 by driving the driving unit 156, as shown in FIG. 5 (S110).

After the angle of the reflection mirror 155 is adjusted, the material property of the third measurement object 30 may be inspected through a process similar to that when the material properties of the first and second measurement objects 10 and 20 are measured.

For example, after the angle of the reflection mirror 155 is adjusted, the light source 110 may provide the first light (L1) to the third measurement unit 140 (S120). The third illumination unit 141 may provide the fourth light (L4) into the third measurement object 30 (S130). The third light receiving unit 142 may provide the third optical signal (S3) to the inspection unit 160 (S140). The inspection unit 160 may inspect the material property of the third measurement object 30 using the third optical signal (S3) (S150). The material property of the third measurement object 30 may be inspected according to the above-described process.

Accordingly, the first light (L1) and the third optical signal (S3) may both travel between the third head 153 and the third measurement unit 140 along the same optical fiber, which may be referred to herein as a third optical fiber. The third optical fiber may be different form both the first optical fiber and the second optical fiber. However, the present disclosure is not limited thereto.

The apparatus for inspecting the material property according to some exemplary embodiments of the present disclosure may inspect material properties of a plurality of measurement objects using the single inspection unit 160, by reflecting light and optical signals by adjusting the angle of the reflection mirror 155 arranged in the measurement position selection unit 150. Accordingly, the time required to inspect the material properties of the plurality of measurement objects can be reduced. In addition, the installation cost can be reduced by inspecting the material properties of the plurality of measurement objects using the single inspection unit 160.

It is to be understood that the material properties of the measurement objects may be measured in one or more of a variety of ways, each involving the use of the incident light (L2, L3, and L4) and the receiving of the resulting light (S1, S2, and S3). For example, the incident light may be light incident upon a surface of the measurement object and the resulting light may be light that is either reflected off of the measurement object, light that has passed through the measurement object, light that has been scattered by the measurement object, or the incident light may excite the atoms of the measurement object and the resulting light might be light that is given off by the atoms of the measurement object as they relax from their excited state. In this way, the resulting light (S1, S2, and S3) may be analyzed by the inspection unit 160 by computer vision and/or spectral analysis.

Hereinbelow, an apparatus for inspecting a material property according to some exemplary embodiments of the present disclosure will be described with reference to FIG. 6. The differences from the inspecting apparatus illustrated in FIG. 1 will be highlighted and it may be assumed that those elements not described with respect to this figure may be at least similar to corresponding elements already described with respect to previous figures.

Figure 6:
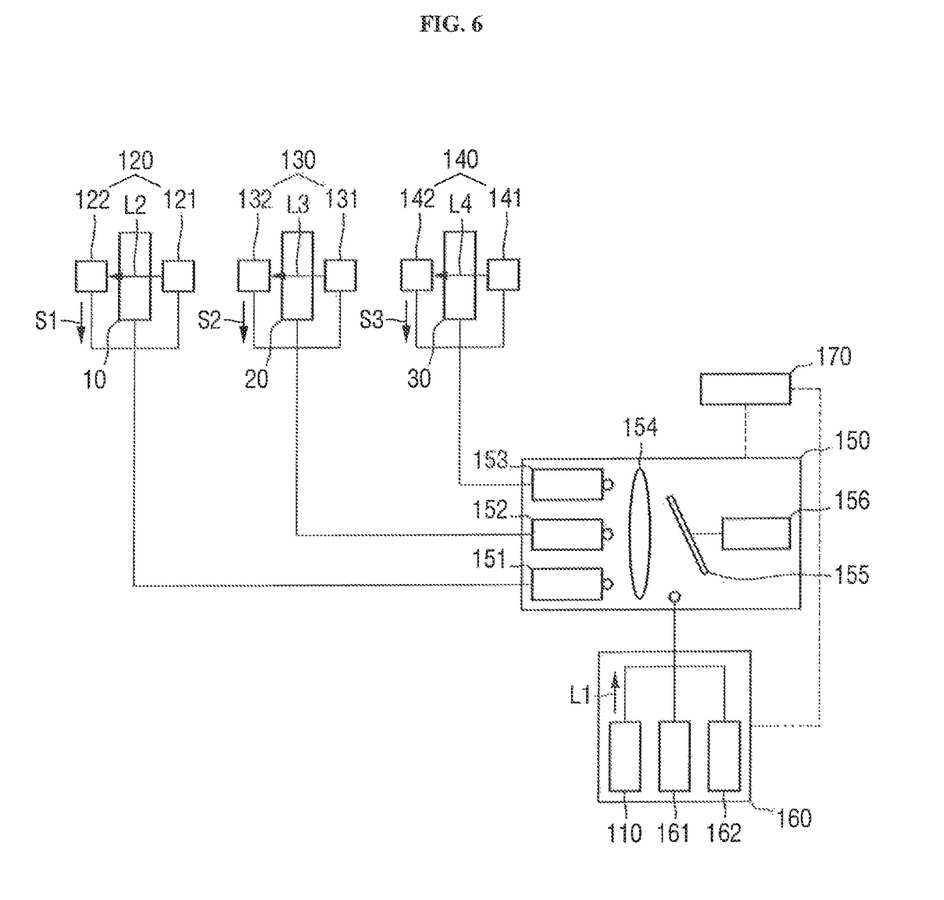
FIG. 6 is a schematic diagram illustrating an apparatus for inspecting a material property according to some exemplary embodiments of the present disclosure.

FIG. 6 is a schematic diagram illustrating an apparatus for inspecting a material property according to some exemplary embodiments of the present disclosure.

Referring to FIG. 6, in the apparatus for inspecting the material property, according to some exemplary embodiments of the present disclosure, the inspection unit 160 may further include a particle measurement unit 162 to inspect a particle size included in each of the first to third measurement objects 10, 20, and 30, in addition to the concentration measurement unit 161 to inspect a concentration of a material included in each of the first to third measurement objects 10, 20, and 30.

Accordingly, the apparatus for inspecting the material property shown in FIG. 6 may inspect different material properties of each of the first to third measurement objects 10, 20, and 30, for example, a concentration of a material and a particle size, simultaneously.

Hereinbelow, an apparatus for inspecting a material property according to some exemplary embodiments of the present disclosure will be described with reference to FIG. 7. The differences from the inspecting apparatus illustrated in FIG. 1 will be highlighted and it may be assumed that those elements not described with respect to this figure may be at least similar to corresponding elements already described with respect to previous figures.

Figure 7:
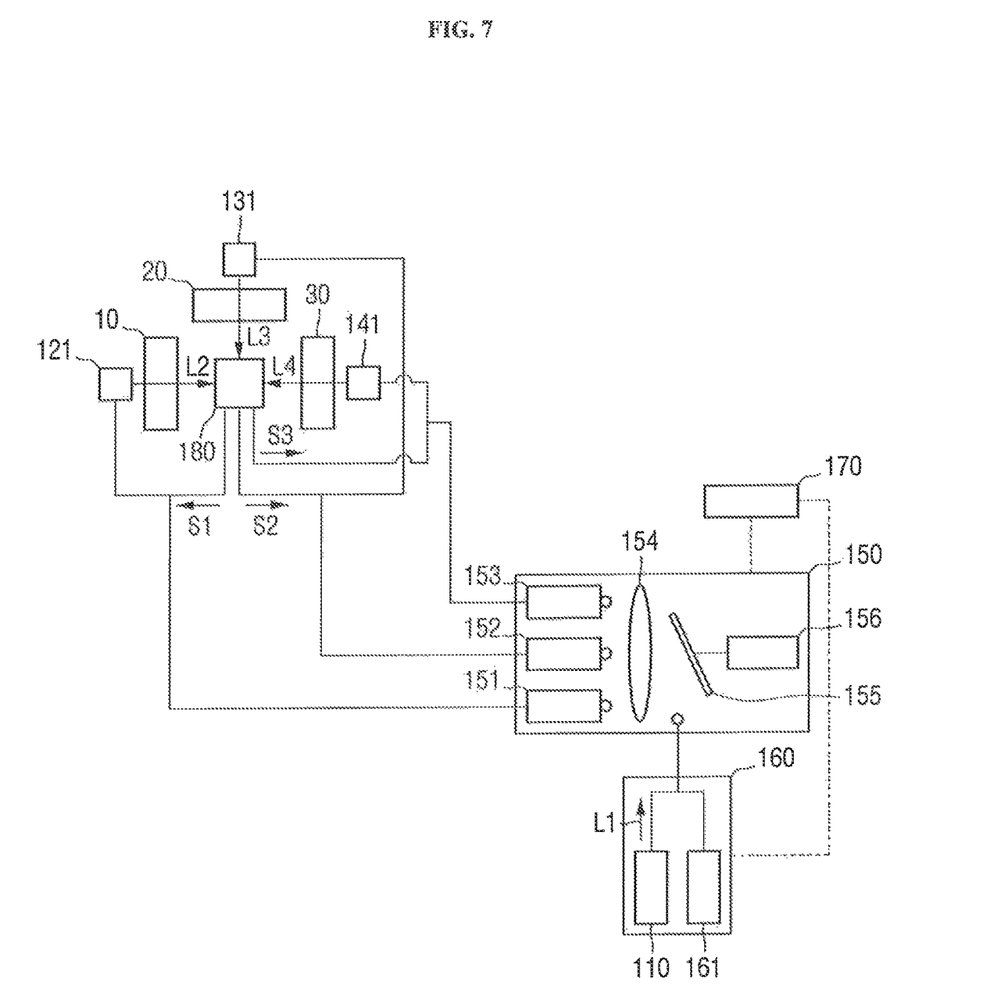
FIG. 7 is a schematic diagram illustrating an apparatus for inspecting a material property according to some exemplary embodiments of the present disclosure.

FIG. 7 is a schematic diagram illustrating an apparatus for inspecting a material property according to some exemplary embodiments of the present disclosure.

Referring to FIG. 7, in the apparatus for inspecting the material property according to some exemplary embodiments of the present disclosure, the second light (L2) directed from the first illumination unit 121 and passing through the first measurement object 10, the third light (L3)

directed from the second illumination unit 131 and passing through the second measurement object 20, and the fourth light (L4) directed from the third illumination unit 141 and passing through the third measurement object 30 may each be collected at a fourth light receiving unit 180, which is a single light receiving unit.

The fourth light receiving unit 180 may receive the second light (L2) passing through the first measurement object 10 and provide the first optical signal (S1) to the measurement position selection unit 150, may receive the third light (L3) passing through the second measurement object 20 and provide the second optical signal (S2) to the measurement position selection unit 150, and may receive the fourth light (LA) passing through the third measurement object 30 and provide the third optical signal (S3) to the measurement position selection unit 150.

Hereinbelow, an apparatus for inspecting a material property according to some exemplary embodiments of the present disclosure will be described with reference to FIG. 8. The differences from the inspecting apparatus illustrated in FIG. 1 will be highlighted and it may be assumed that those elements not described with respect to this figure may be at least similar to corresponding elements already described with respect to previous figures.

Figure 8:
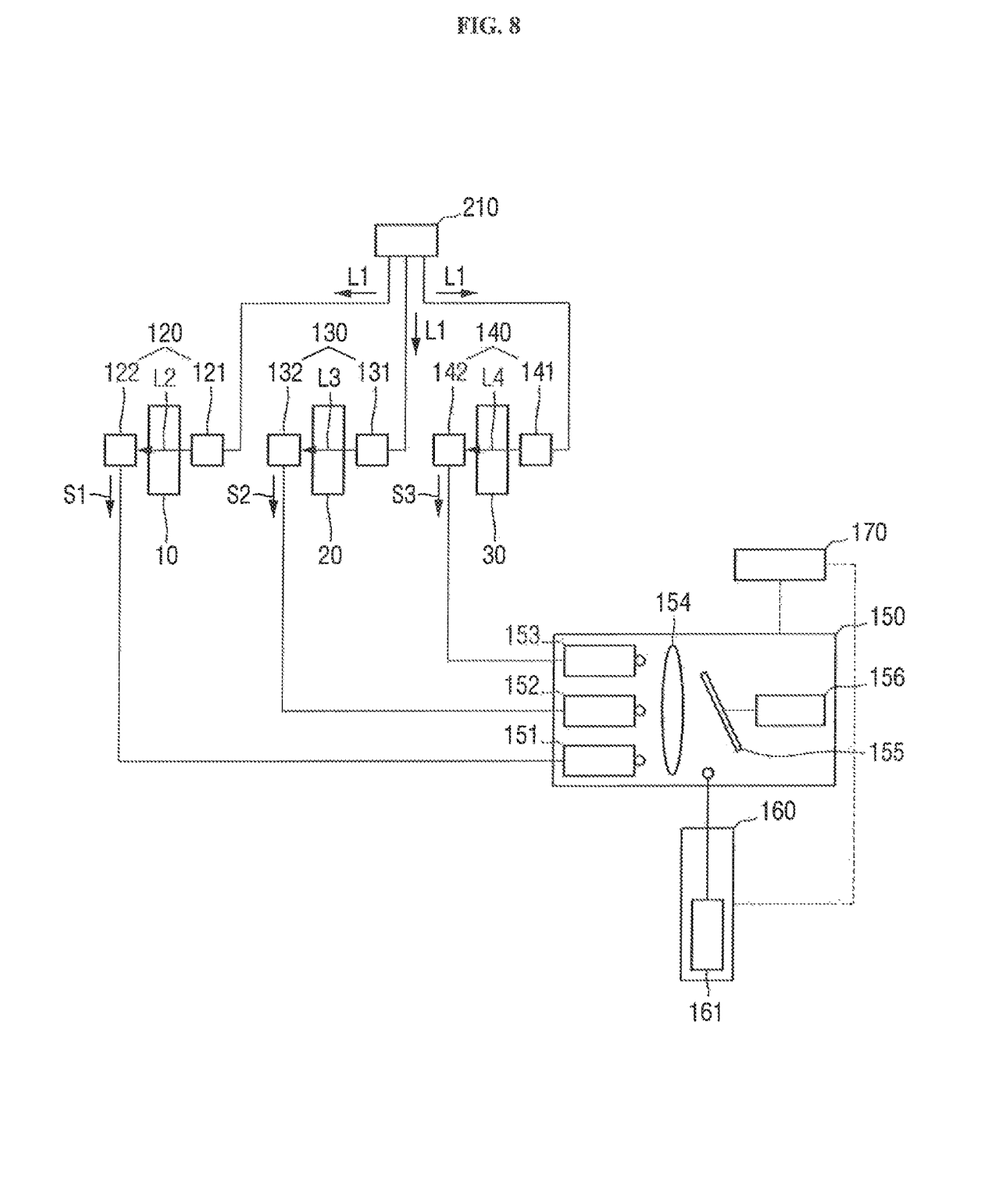
FIG. 8 is a view schematic diagram an apparatus for inspecting a material property according to some exemplary embodiments of the present disclosure.

FIG. 8 is a schematic diagram illustrating an apparatus for inspecting a material property according to some exemplary embodiments of the present disclosure.

Referring to FIG. 8, in the apparatus for inspecting the material property according to some exemplary embodiments of the present disclosure, a light source 210 may be disposed outside of the inspection unit 160.

For example, the light source 210 may provide the first light (L1) to each of the first illumination unit 121, the second illumination unit 131, and the third illumination unit 141 without going through the reflection mirror 155. In this case, each of the first illumination unit 121, the second illumination unit 131, and the third illumination unit 141 might not be connected to the measurement position selection unit 150.

After the light source 210 provides the first light (L1) to any one of the first illumination unit 121, the second illumination unit 131, and the third illumination unit 141, the control unit 170 may provide any one of the first optical signal (S1), the second optical signal (S2), and the third optical signal (S3) to the inspection unit 160 by adjusting the angle of the reflection mirror 155.

For example, when the first illumination unit 121 receives the first light (L1) from the light source 210 and directs the second light (L2) into the first measurement object 10, the control unit 170 may provide the first optical signal (S1) to the inspection unit 160 by adjusting the angle of the reflection mirror 155. When the second illumination unit 131 receives the first light (L1) from the light source 210 and directs the third light (L3) into the second measurement object 20, the control unit 170 may provide the second optical signal (S2) to the inspection unit 160 by adjusting the angle of the reflection mirror 155. When the third illumination unit 141 receives the first light (L) from the light source 210 and directs the fourth light (L4) into the third measurement object 30, the control unit 170 may provide the third optical signal (S3) to the inspection unit 160 by adjusting the angle of the reflection mirror 155.

Hereinbelow, an apparatus for inspecting a material property according to some exemplary embodiments of the present disclosure will be described with reference to FIG. 9. The differences from the inspecting apparatus illustrated in FIG. 1 will be highlighted and it may be assumed that those elements not described with respect to this figure may be at least similar to corresponding elements already described with respect to previous figures.

Figure 9:
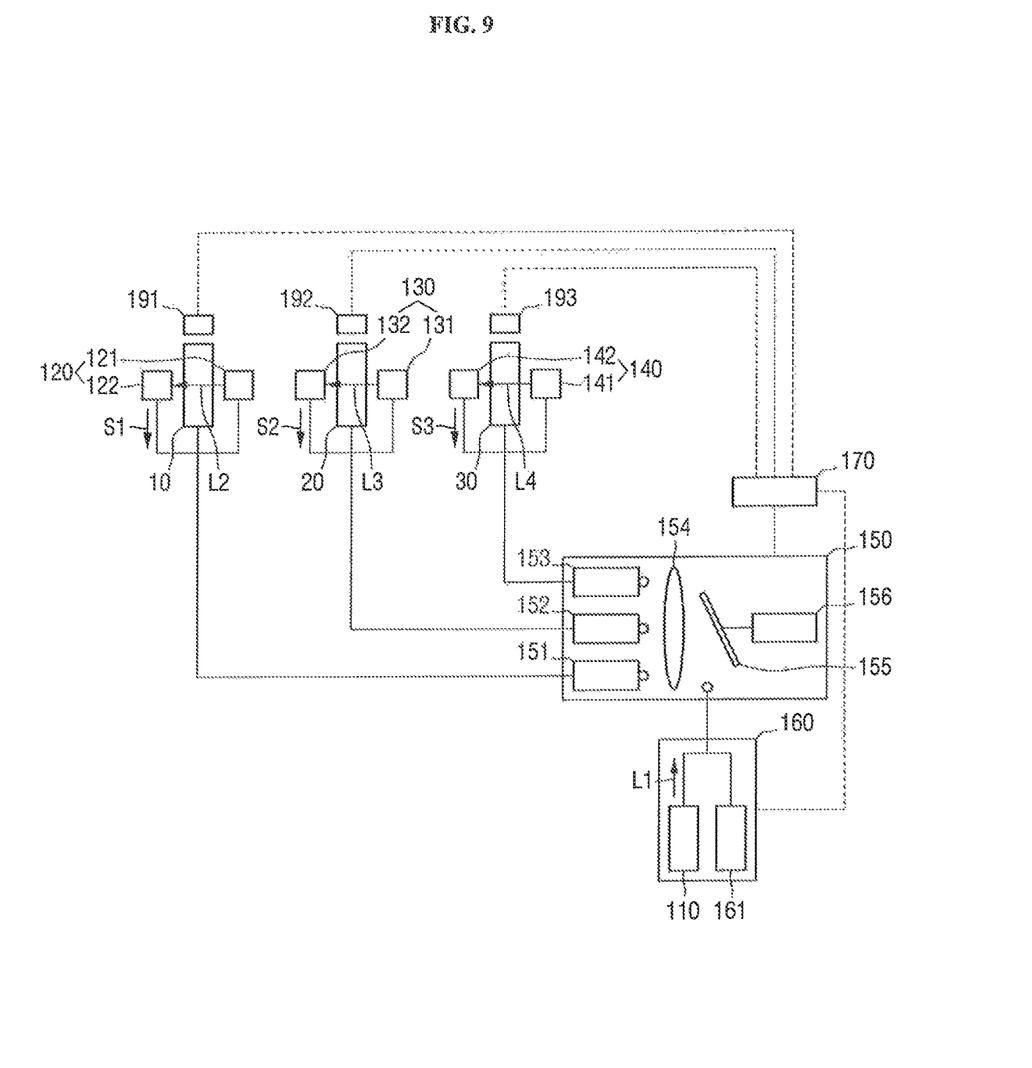
FIG. 9 is a schematic diagram illustrating an apparatus for inspecting a material property according to some exemplary embodiments of the present disclosure.

FIG. 9 is a schematic diagram illustrating an apparatus for inspecting a material property according to some exemplary embodiments of the present disclosure.

Referring to FIG. 9, the apparatus for inspecting the material property according to some exemplary embodiments of the present disclosure may further include a first position sensor 191, a second position sensor 192, and a third position sensor 193.

The first position sensor 191 may sense the first measurement object 10 positioned in the first measurement unit 120. The first position sensor 191 may provide a first position signal to the control unit 170 when the first measurement object 10 is positioned in the first measurement unit 120.

When the first position signal is received from the first position sensor 191, the control unit 170 may provide the first light (L1) provided from the light source 110 to the first illumination unit 121 by adjusting the angle of the reflection mirror 155, and may provide the first optical signal (S1) provided from the first light receiving unit 122 to the inspection unit 160.

The second position sensor 192 may sense the second measurement object 20 positioned in the second measurement unit 130. The second position sensor 192 may provide a second position signal to the control unit 170 when the second measurement object 20 is positioned in the second measurement unit 130.

When the second position signal is received from the second position sensor 192, the control unit 170 may provide the first light (L1) provided from the light source 110 to the second illumination unit 131 by adjusting the angle of the reflection mirror 155, and may provide the second optical signal (S2) provided from the second light receiving unit 132 to the inspection unit 160.

The third position sensor 193 may sense the third measurement object 30 positioned in the third measurement unit 140. The third position sensor 193 may provide a third position signal to the control unit 170 when the third measurement object 30 is positioned in the third measurement unit 140.

When the third position signal is received from the third position sensor 193, the control unit 170 may provide the first light (L1) provided from the light source 110 to the third illumination unit 141 by adjusting the angle of the reflection mirror 155, and may provide the third optical signal (S3) provided from the third light receiving unit 142 to the inspection unit 160.

In this way, the measurement position selection unit 150 may be able to automatically optically connect the correct measurement unit with single inspection unit 160 so as to test the measurement object that is present.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:
1. An inspection apparatus, comprising:
a light source generating a first light;
a first measurement unit configured to receive the first light from the light source and direct the first light to a first measurement object;

a second measurement unit configured to receive the first light from the light source and direct the first light to a second measurement object which is different from the first measurement object;

an inspection unit configured to receive a first optical signal provided from the first measurement unit along a first optical path and inspect the first measurement object using the first optical signal, and to receive a second optical signal provided from the second measurement unit along a second optical path that is different from the first optical path and inspect the second measurement object using the second optical signal; and a measurement position selection unit configured to alternately enable the first and second optical paths by adjusting an angle of a reflection mirror such that when the measurement position selection unit enables the first optical path, the first light travels through the first measurement object before it is received by the inspection unit and the measurement position selection unit enables the second optical path, the first light travels through the second measurement object before it is received by the inspection unit.

2. The apparatus of claim 1, wherein the first measurement unit comprises a first illumination unit configured to direct the first light into the first measurement object, and a first light receiving unit configured to receive the first light passing through or reflecting off of the first measurement object and provide the first optical signal to the measurement position selection unit, and wherein the second measurement unit comprises a second illumination unit configured to direct the first light into the second measurement object, and a second light receiving unit configured to receive the first light passing through or reflecting off of the second measurement object and provide the second optical signal to the measurement position selection unit.

3. The apparatus of claim 1, further comprising:
a driving unit configured to change the angle of the reflection mirror; and
a control unit configured to control the driving unit to adjust the angle of the reflection mirror.

4. The apparatus of claim 3, wherein the control unit is configured to drive the driving unit according to a preset time and provide the first or second optical signals to the inspection unit.

5. The apparatus of claim 1, further comprising a control unit configured to:
provide the first optical signal to the inspection unit by adjusting the angle of the reflection mirror when the first measurement unit directs the first into the first measurement object; and
provide the second optical signal to the inspection unit by adjusting the angle of the reflection mirror when the second measurement unit directs the first light into the second measurement object.

6. The apparatus of claim 1, further comprising a lens configured to concentrate the first or second optical signals on the reflection mirror.

7. The apparatus of claim 1, wherein the inspection unit comprises a concentration measurement unit configured to measure a concentration of a material included in the first or second measurement objects.

8. The apparatus of claim 1, wherein the inspection unit comprises a particle measurement unit configured to measure a particle size included in the first or second measurement objects.

9. The apparatus of claim 1, further comprising a third light receiving unit configured to:
receive the first light passing through the first measurement unit and provide the first optical signal to the measurement position selection unit; and
receive the first light passing through the second measurement object and provide the second optical signal to the measurement position selection unit.

10. An inspection apparatus, comprising:
a first measurement unit configured to direct a light into a first measurement object;
a second measurement unit configured to direct the light into a second measurement object;
an inspection unit configured to inspect the first measurement object and inspect the second measurement object; and
a measurement position selection unit configured to alternatively provide a first optical signal of the light from the first measurement unit, through the first measurement object, and to the inspection unit and a second optical signal of the light from the second measurement unit, through the second measurement object, and to the inspection unit, by adjusting an angle of a reflection mirror.

11. The apparatus of claim 10, wherein the first measurement unit comprises a first illumination unit configured to direct the light into the first measurement object, and a first light receiving unit configured to receive the light passing through the first measurement object and provide the first optical signal to the measurement position selection unit, and wherein the second measurement unit comprises a second illumination unit configured to direct the light into the second measurement object, and a second light receiving unit configured to receive the light passing through the second measurement object and provide the second optical signal to the measurement position selection unit.

12. The apparatus of claim 10, wherein the inspection unit is configured to determine a concentration of a material or a particle size.

13. The apparatus of claim 10, further comprising;
a driving unit configured to change the angle of the reflection mirror; and
a control unit configured to control the driving unit to adjust the angle of the reflection mirror.

14. The apparatus of claim 10, further comprising a lens configured to concentrate the first and second optical signals on the reflection mirror.

* * * * *